United States Patent [19]

Harandi et al.

[11] Patent Number: 5,625,113

[45] Date of Patent: *Apr. 29, 1997

[54] ISOPARAFFIN/OLEFIN ALKYLATION

[75] Inventors: Mohsen N. Harandi, Langhorne, Pa.; James H. Beech, Jr., Wilmington, Del.; Albin Huss, Jr., Chadds Ford, Pa.; Robert A. Ware, Wyndmoor, Pa.; Altaf Husain, Marlton, N.J.

[73] Assignee: Mobil Oil Corporation, Fairfax, Va.

[*] Notice: The term of this patent shall not extend beyond the expiration date of Pat. No. 5,258,569.

[21] Appl. No.: 365,334

[22] Filed: Dec. 28, 1994

Related U.S. Application Data

[63] Continuation of Ser. No. 142,036, Oct. 28, 1993, abandoned.

[51] Int. Cl.$^6$ ........................................ C07C 2/58
[52] U.S. Cl. ................. 585/722; 585/714; 585/716; 585/730; 585/731
[58] Field of Search ........................ 585/714, 716, 585/722, 730, 731

[56] References Cited

U.S. PATENT DOCUMENTS

| | | | |
|---|---|---|---|
| 3,251,902 | 5/1966 | Garwood et al. | 260/683.64 |
| 3,467,728 | 9/1969 | Hervert | 260/683.2 |
| 3,644,565 | 2/1972 | Biale | 260/683.43 |
| 3,647,916 | 3/1972 | Caesar et al. | 260/683.43 |
| 3,655,813 | 4/1972 | Kirsch et al. | 260/683.43 |
| 3,717,686 | 2/1973 | Miller | 585/730 |
| 3,738,977 | 6/1973 | Biale | 260/94.9 |
| 3,855,342 | 12/1974 | Huang et al. | 260/683.44 |
| 3,855,345 | 12/1974 | Hutson, Jr. et al. | 585/716 |
| 3,893,942 | 7/1975 | Yang | 252/411 |
| 3,917,738 | 11/1975 | Fenske et al. | 260/683.43 |
| 4,384,161 | 5/1983 | Huang | 585/722 |
| 4,992,615 | 2/1991 | Huss et al. | 585/722 |
| 5,191,148 | 3/1993 | Degnan et al. | 585/724 |
| 5,236,575 | 8/1993 | Bennett et al. | 585/407 |
| 5,258,569 | 11/1993 | Chu et al. | 585/722 |
| 5,304,698 | 4/1994 | Husain | 585/722 |

FOREIGN PATENT DOCUMENTS 1593716  7/1970  France.

OTHER PUBLICATIONS

"Modern Alkylation", by Lyle F. Albright, *Oil and Gas Journal*, Nov. 12 & 26, 1990.

*Primary Examiner*—Asok Pal
*Attorney, Agent, or Firm*—Ronald A. Bleeker; Robert B. Furr, Jr.; Thomas W. Steinberg

[57] ABSTRACT

A process is disclosed for alkylating an isoparaffin with an olefin comprising the steps of:

(a) reacting an isoparaffin having from 4 to 8 carbon atoms with an olefin having from 2 to 12 carbon atoms in a first alkylation reaction stage at temperature from about −40° C. to about 500° C. and overall isoparaffin:olefin feed weight ratio of from about 1:1 to about 250:1 with a solid alkylation catalyst comprising a synthetic porous crystalline material characterized by an X-ray diffraction pattern including values substantially as set forth in Table I of the specification and having a composition comprising the molar relationship $$X_2O_3:(n)YO_2,$$

wherein n is less than about 35, X is a trivalent element and Y is a tetravalent element;

(b) mixing the effluent from said first alkylation stage with additional olefin to evolve an intermediate stream having an isoparaffin:olefin weight ratio of from about 2:1 to about 100:1; and (c) reacting said intermediate stream in a second alkylation stage in the absence of intermediate fractionation with a liquid acid catalyst comprising $H_2SO_4$ to produce $C_5+$ alkylate.

21 Claims, 1 Drawing Sheet

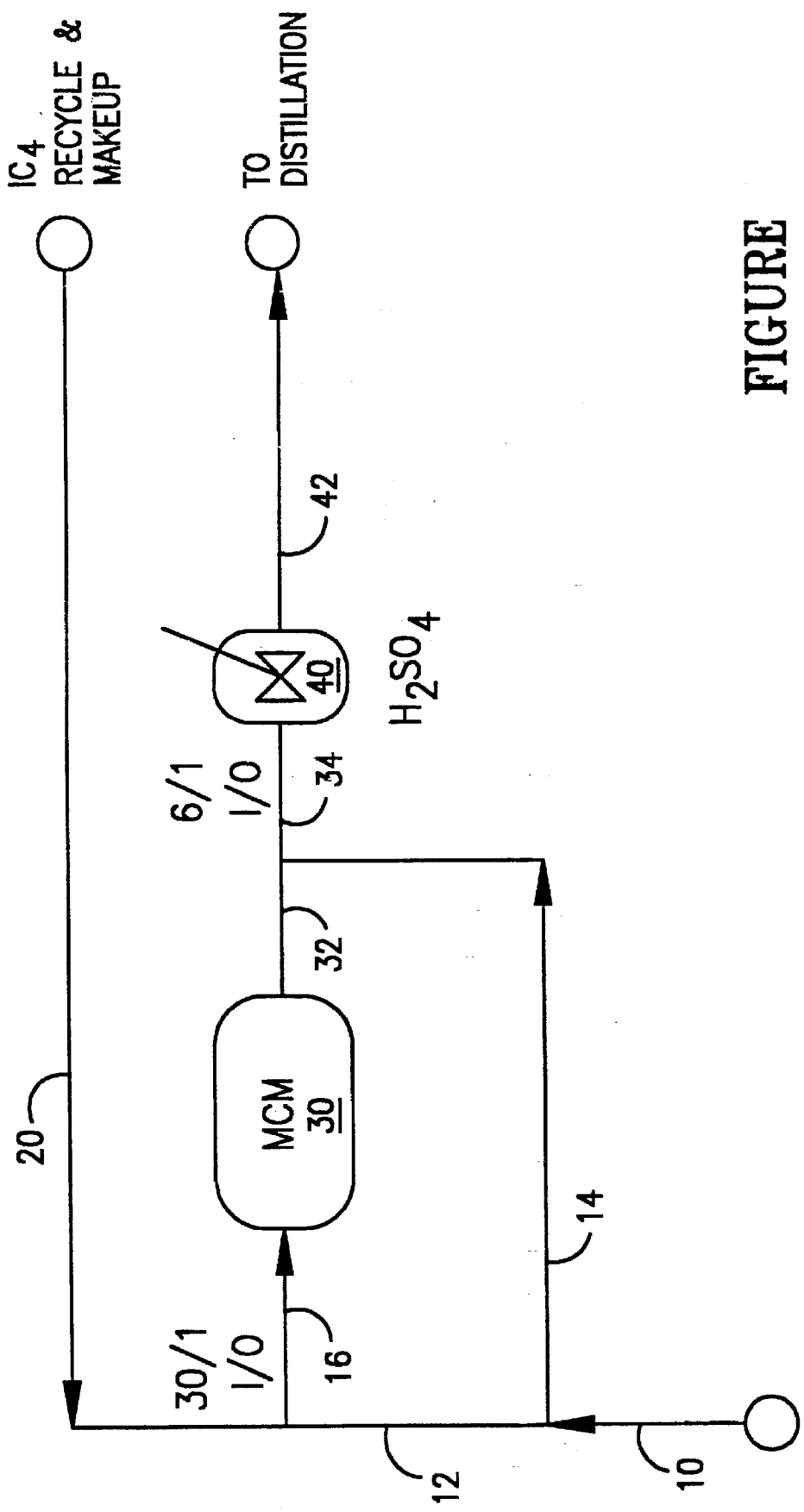
FIGURE

ISOPARAFFIN/OLEFIN ALKYLATION

This is a continuation of application Ser. No. 08/142,036, filed on Oct. 28, 1993, now abandoned.

FIELD OF THE INVENTION

The present invention relates to the art of improving octane rating of gasoline by alkylating an isoparaffin with an olefin. Particularly, this invention relates to a two-stage sequential alkylation process using, as catalysts, a porous synthetic crystalline material designated as MCM-49 in a first reaction stage and sulfuric acid in a second reaction stage.

BACKGROUND OF THE INVENTION

This invention results from a need to improve octane ratings for gasoline. Isoparaffin-olefin alkylation is a means to produce highly branched paraffins which affect this octane improvement.

Alkylation is a reaction in which an alkyl group is added to an organic molecule. Thus, an isoparaffin can be reacted with an olefin to provide an isoparaffin of higher molecular weight. Industrially, the concept depends on the reaction of a $C_2$ to $C_5$ olefin with isobutane in the presence of an acidic catalyst producing a so-called alkylate, a valuable blending component in the manufacture of gasolines because of its high octane rating.

Traditionally, the process in the industry includes the use of hydrofluoric acid or sulfuric acid as a catalyst carried out under controlled temperature conditions. Low temperatures are utilized in the sulfuric acid process to minimize the side reaction of olefin polymerization and the acid strength is generally maintained at 88 to 94% by the continuous addition of fresh acid and the continuous withdrawal of spent acid. The hydrofluoric acid process is less temperature-sensitive and the acid is easily recovered and purified.

The typical types of alkylation currently used to produce high octane blending components, that is, the hydrofluoric acid and sulfuric acid alkylation processes, have inherent drawbacks including environmental concerns, acid consumption and sludge disposal. With the increasing demands for octane and the increasing environmental concerns, it has been desirable to develop an alkylation process based on a catalyst system which can meet product quality demands, while at the same time minimizing safety and environmental problems.

U.S. Pat. No. 3,644,565 discloses alkylation of a paraffin with an olefin in the presence of a catalyst comprising a Group VIII noble metal present on a crystalline aluminosilicate zeolite. The catalyst is pretreated with hydrogen to promote selectivity.

U.S. Pat. No. 3,647,916 describes an isoparaffin-olefin alkylation process featuring use of an ion-exchanged crystalline aluminosilicate, isoparaffin/olefin molar ratios below 3:1 and regeneration of the catalyst.

U.S. Pat. No. 3,655,813 discloses a process for alkylating $C_4$–$C_5$ isoparaffins with $C_3$–$C_9$ olefins using a crystalline aluminosilicate zeolite catalyst wherein a halide adjuvant is used in the alkylation reactor. The isoparaffin and olefin are introduced into the alkylation reactor at specified concentrations and catalyst is continuously regenerated outside the alkylation reactor.

U.S. Pat. No. 3,236,671 discloses an alkylation reaction wherein crystalline aluminosilicate zeolites having silica to alumina mole ratios above 3 are used. The reference also discloses the use of various metals exchanged and/or impregnated on such zeolites.

U.S. Pat. No. 3,738,977 discloses alkylation of paraffins with ethylene using a zeolite catalyst which possesses a Group VII metal component. The catalyst is pretreated with hydrogen.

U.S. Pat. No. 3,917,738 describes a process for alkylating an isoparaffin with an olefin using a solid, particulate catalyst capable of absorbing the olefin. The isoparaffin and the olefin are admixed to form a reactant stream in contact with catalyst particles at the upstream end of an adsorption zone. Thereafter, the reactants are passed concurrently with the catalyst so that a controlled amount of olefin is adsorbed into the catalyst before the combination of reactants and catalyst is introduced into an alkylation zone. This controlled olefin adsorption is thought to prevent polymerization of the olefin during alkyation.

U.S. Pat. No. 4,384,161 describes a process of alkylating isoparaffins with olefins to provide alkylate using a large-pore zeolite catalyst capable of absorbing 2,2,4-trimethylpentane, for example, ZSM-4, ZSM-20, ZSM-3, ZSM-18, zeolite Beta, faujasite, mordenite, zeolite Y and the rare earth metal-containing forms thereof, and a Lewis acid such as boron trifluoride, antimony pentafluoride or aluminum trichloride. The use of a large-pore zeolite with a Lewis acid is reported to increase the activity and selectivity of the zeolite, thereby effecting alkylation with high olefin space velocity and low isoparaffin:olefin ratio.

In the past, severe activity and stability problems have been noted with respect to zeolite-based alkylation catalyst systems. U.S. Pat. Nos. 3,251,902 and 3,893,942, as well as French Patent 1,593,716, and the article by Kirsh and Potts, *Div. of Pet. Chem. A.C.S.*, 15, A109 (1970), exemplify these problems. Improved stability was noted when a Lewis acid such as $BF_3$ was used in combination with macroreticular acid cation exchange resins as pointed out in U.S. Pat. No. 3,855,342. More recently, U.S. Pat. No. 4,384,161 has disclosed the use of $BF_3$ in combination with large pore zeolites such as ZSM-4 and Beta to effectively catalyze isoparaffin/olefin alkylation reactions.

U.S. Pat. No. 3,467,728 relates to a process for isomerizing olefinic hydrocarbon, such as 1-butene or 1-pentene, by contacting the hydrocarbon with a catalyst comprising a crystalline alumina silicate combined with a substantially anhydrous boron halide.

The two-part article, "Modern Alkylation", by Lyle F. Albright, *Oil and Gas Journal*, Nov. 12 and 26, 1990, summarizes the state of the art in alkylation technology, and highlights problems associated with various liquid catalyst systems, further emphasizing the desirability of developing a commercially viable isoparaffin/olefin alkylation process employing a promoted solid catalyst.

U.S. Pat. No. 5,191,148 to Degnan et al. teaches a process for alkylating an isoparaffin with an olefin in the presence of a synthetic porous material designated as MCM-41. Each of the preceeding references is incorporated by reference as if set forth at length herein.

SUMMARY OF THE INVENTION

This invention provides a two-stage isoparaffin/olefin alkylation process. The process employs two catalysts in sequence, both of which have been found to independently produce undesirable $C_9$+ byproducts from the reaction of isoparaffins with olefins. The process of this invention reacts a mixed isoparaffin/olefin feed with each of these two catalysts in sequence, and the resulting product contains less of the undesired $C_9+$ byproducts than a conventional single stage isoparaffin/olefin alkylation process using a strong Brønsted acid catalyst such as $H_2SO_4$. Because the $C_9+$ fraction is less less valuable than the $C_8$ alkylate, even a seemingly minor reduction in the rate of $C_9+$ product is an important advance in the art of catalytic isoparaffin/olefin alkylation. Further, the two-stage process of this invention operates at relatively low overall excess isoparaffin ratios, thus reducing the costs associated with separating and recycling large volumes of isoparaffin which are typically required in solid-catalyzed isoparaffin-olefin alkylation processes.

The present invention provides an isoparaffin/olefin alkylation process comprising the steps of:

(a) reacting an isoparaffin having from 4 to 8 carbon atoms with an olefin having from 2 to 12 carbon atoms in a first alkylation reaction stage at temperature from about −40° C. to about 500° C. and overall isoparaffin:olefin feed weight ratio of from about 1:1 to about 250:1 with a solid alkylation catalyst comprising a synthetic porous crystalline material characterized by an X-ray diffraction pattern including values substantially as set forth in Table I of the specification and having a composition comprising the molar relationship $$X_2O_3:(n)YO_2,$$

wherein n is less than about 35, X is a trivalent element and Y is a tetravalent element;

(b) mixing the effluent from said first alkylation stage with additional olefin to evolve an intermediate stream having an isoparaffin:olefin weight ratio of from about 2:1 to about 100:1

(c) reacting said intermediate stream in a second alkylation stage in the absence of intermediate fractionation with a liquid acid catalyst comprising $H_2SO_4$ to produce $C_5+$ alkylate.

The term "overall isoparaffin:olefin feed weight ratio" as used herein refers to the isoparaffin:olefin ratio in the total feed to an alkylation reaction zone, including both fresh and recycled isoparaffin.

In a preferred embodiment, additional olefin is added to the first alkylation stage effluent before it enters the second reaction stage to provide a markedly lower overall isoparaffin:olefin ratio in the second reaction stage than in the first reaction stage. Olefin conversion in both stages typically exceeds 90%, and essentially complete olefin conversion is preferred.

BRIEF DESCRIPTION OF THE DRAWING

The FIGURE is a simplified flow schematic showing the major processing steps of one embodiment of the present invention.

DETAILED DESCRIPTION

Alkylate is a particularly valuable portion of the gasoline pool, as it has both high research and motor octane, contains no olefins or aromatics and little or no sulfur, demonstrates excellent stability, and is clean burning. The present process, therefore, not only produces a superior motor fuel blending component, but also improves refinery safety and reliability while minimizing environmental concerns (e.g., liquid acid inventory) historically associated with the manufacture of alkylate gasolines.

The present process further overcomes the problem of excessively high feed isoparaffin:olefin ratios which has, in the past, been associated with solid-catalyzed isoparaffin/olefin alkylation processes.

Feedstocks

Feedstocks useful in the present alkylation process include at least one isoparaffin and at least one olefin. The isoparaffin reactant used in the present alkylation process has from about 4 to about 8 carbon atoms. Representative examples of such isoparaffins include isobutane, 3-methylhexane, 2-methylhexane, 2,3-dimethylbutane and 2,4-dimethylhexane.

The olefin component of the feedstock includes at least one olefin having from 2 to 12 carbon atoms. Representative examples of such olefins include butene-2, isobutylene, butene-1, propylene, ethylene, hexene, octene, and heptene, merely to name a few. The preferred olefins include the $C_4$ olefins, for example, butene-1, butene-2, isobutylene, or a mixture of one or more of these $C_4$ olefins, with butene-2 being the most preferred. Suitable feedstocks for the process of the present invention are described in U.S. Pat. No. 3,862,258 to Huang et al. at column 3, lines 44–56, the disclosure of which is incorporated by reference as if set forth at length herein.

The molar ratio of isoparaffin to olefin is generally from about 1:1 to about 250:1, preferably from about 1:1 to about 50:1, and more preferably from about 5:1 to about 25:1.

Process Conditions

The first and second reaction stages of the present alkylation process are suitably conducted at temperatures of from about −40° to about 500° C., preferably from about 0° to about 200° C., and more preferably below about 150° C. to avoid undesirable side reactions. The first stage typically operates at higher temperatures within this range, for example, from about 50° to about 200° C. Lower reaction temperatures are preferred in the second reaction stage to maximize alkylate octane. For example, temperatures as low as −20° C. may be effectively employed in the second reaction stage. Operating temperature in the second reaction stage typically falls within the range of about −20° to about 100° C., with the most preferred operating temperatures falling within the range of about −20° to about 40° C.

Operating pressure in both reaction stages is generally controlled to maintain the reactants in the liquid phase, and is suitably from about 50 to about 1500 psig, preferably from about 200 to about 900 psig.

The isoparaffin:olefin weight ratio in the first reaction stage typically falls within the range of from about 1:1 to about 250:1, preferably from about 5:1 to about 100:1, and more preferably from about 10:1 to about 50:1. In a particularly preferred embodiment, the isoparaffin:olefin ratio in the total feed to the first reaction stage is about 30:1.

The isoparaffin:olefin weight ratio in the second reaction stage typically falls within the range of from about 1:1 to about 100:1, preferably from about 2:1 to about 20:1, and more preferably from about 2:1 to about 10:1. In a particularly preferred embodiment, the isoparaffin:olefin ratio in the total feed to the second reaction stage is about 6:1.

The particular operating conditions used in the present process will depend on the specific alkylation reaction. Process conditions such as temperature, pressure, space velocity and molar ratio of the reactants will affect the characteristics of the resulting alkylate, and may be adjusted within the disclosed ranges by those skilled in the art with only minimal trial and error.

Supplemental isoparaffin may optionally be added to the second reaction stage. The supplemental isoparaffin may be mixed with the effluent from the first reaction stage, or may be charged directly to the second reaction stage. Because the present process inherently requires less excess isoparaffin than typical solid-catalyzed alkylation processes, the interstage isoparaffin addition is generally not required to produce commercial quality alkylate product.

In a preferred embodiment of the present invention, essentially all of the olefin feed to the first alkylation reaction stage reacts, either to form isoparaffinic alkylate or olefinic oligomerate. Additional olefin is then mixed with the first alkylation stage effluent before it enters the second reaction stage to provide a lower isoparaffin:olefin ratio in the second reaction stage than that of the first alkylation reaction stage. In a more preferred embodiment, the process alkylates isobutane with n-butenes, with 2-butenes being particularly preferred. The feedstock at the inlet of the first alkylation stage thus most preferably comprises isobutane and 2-butene in an isobutane:2-butene ratio of about 30:1, and additional 2-butene is added to the effluent stream from the first reaction zone to provide a second alkylation stage feed with a total isobutane:olefin ratio of about 6:1.

The effluent from the first reaction stage preferably flows to the second reaction stage with no intermediate fractionation. For isobutane/butenes alkylation, avoiding the intermediate fractionation not only appears to improve selectivity for the desired trimethylpentanes, but also suppresses the production of undesired $C_9+$ side products. In a preferred embodiment, olefin-containing feed is added between the first and second reaction stages.

As used herein, the term "first reaction stage" refers to a solid-catalyzed alkylation reaction stage and the term "second reaction stage" refers to the ($H_2SO_4$) liquid-catalyzed alkylation reaction stage. The solid-catalyzed alkylation reaction stage may comprise one reaction zone, or a plurality of reaction zones in parallel or series. Similarly, the liquid-catalyzed reaction stage may comprise one reaction zone, or may also comprise several reaction zones connected in parallel or series.

The process of this invention employs a first solid catalyst as described herein. In a particularly preferred embodiment, the solid catalyst comprises the porous crystalline material named MCM-49 as described in U.S. Pat. No. 5,236,575 to Bennett et al., which is incorporated by reference as if set forth at length herein. The calcined form of MCM-49 transforms to a material not readily distinguishable from calcined crystalline material MCM-22 described in U.S. Pat. No. 4,954,325. MCM-49 does not appear to contain all the components apparently present in the PSH-3 composition described in U.S. Pat. No. 4,439,409. MCM-49 as described herein is not contaminated with ZSM-12 or ZSM-5. The calcination transformation product exhibits unusual sorption capacities and unique catalytic utility when compared to PSH-3 synthesized in accordance with U.S. Pat. No. 4,439,409. It exhibits unique catalytic utility when compared to MCM-22 synthesized as taught in U.S. Pat. No. 4,954,325.

MCM-49 has a composition involving the molar relationship:

$$X_2O_3:(n)YO_2,$$

wherein X is a trivalent element, such as aluminum, boron, iron and/or gallium, preferably aluminum; Y is a tetravalent element such as silicon and/or germanium, preferably silicon; and n is less than about 35, e.g. from 2 to less than about 35, usually from about 10 to less than about 35, more usually from about 15 to about 31. In the as-synthesized form, the material has a formula, on an anhydrous basis and in terms of moles of oxides per n moles of $YO_2$, as follows:

$$(0.1-0.6)M_2O:(1-4)R:X_2O_3:nYO_2$$

wherein M is an alkali or alkaline earth metal, and R is an organic moiety. The M and R components are associated with the material as a result of their presence during crystallization, and are easily removed by post-crystallization methods hereinafter more particularly described.

The crystalline material MCM-49 is thermally stable and in the calcined form exhibits high surface area (greater than 400 $m^2/gm$) and unusually large sorption capacity when compared to previously described materials such as calcined PSH-3 and SSZ-25 having similar X-ray diffraction patterns. To the extent desired, the original sodium cations of the as-synthesized material can be replaced in accordance with techniques well known in the art, at least in part, by ion exchange with other cations. Preferred replacing cations include metal ions, hydrogen ions, hydrogen precursor, e.g. ammonium, ions and mixtures thereof. Particularly preferred cations are those which tailor the catalytic activity for certain hydrocarbon conversion reactions. These include hydrogen, rare earth metals and metals of Groups IIA, IIIA, IVA, IB, IIB, IIIB, IVB and VIII of the Periodic Table of the Elements.

In the as-synthesized form, the crystalline MCM-49 material of the invention appears to be a single crystalline phase. It can be prepared in essentially pure form with little or no detectable impurity crystal phases and has an X-ray diffraction pattern which is distinguished from the patterns of other known as-synthesized or thermally treated crystalline materials by the lines listed in Table I below:

TABLE I

| Interplanar d-Spacing (A) | Relative Intensity, I/Io × 100 |
| --- | --- |
| 13.15 ± 0.26 | w–s* |
| 12.49 ± 0.24 | vs |
| 11.19 ± 0.22 | m–s |
| 6.43 ± 0.12 | w |
| 4.98 ± 0.10 | w |
| 4.69 ± 0.09 | w |
| 3.44 ± 0.07 | vs |
| 3.24 ± 0.06 | w |

*shoulder

The X-ray diffraction peak at 13.15±0.26 Angstrom Units (A) is usually not fully resolved for MCM-49 from the intense peak at 12.49±0.24, and is observed as a shoulder of this intense peak. For this reason, the precise intensity and position of the 13.15±0.26 Angstroms peak are difficult to determine within the stated range.

In its calcined form, the crystalline MCM-49 material of the invention transforms to a single crystal phase with little or no detectable impurity crystal phases having an X-ray diffraction pattern which is not readily distinguished from that of MCM-22, but distinguishable from the patterns of other known crystalline materials. The X-ray diffraction pattern of the calcined form of MCM-49 includes the lines listed in Table II below:

TABLE II

| Interplanar d-Spacing (A) | Relative Intensity, I/Io × 100 |
| --- | --- |
| 12.41 ± 0.24 | vs |
| 11.10 ± 0.22 | s |
| 8.89 ± 0.17 | m–s |
| 6.89 ± 0.13 | w |

TABLE II-continued

| Interplanar d-Spacing (A) | Relative Intensity, I/Io × 100 |
|---|---|
| 6.19 ± 0.12 | m |
| 6.01 ± 0.12 | w |
| 5.56 ± 0.11 | w |
| 4.96 ± 0.10 | w |
| 4.67 ± 0.09 | w |
| 4.59 ± 0.09 | w |
| 4.39 ± 0.09 | w |
| 4.12 ± 0.08 | w |
| 4.07 ± 0.08 | w–m |
| 3.92 ± 0.08 | w–m |
| 3.75 ± 0.07 | w–m |
| 3.57 ± 0.07 | w |
| 3.43 ± 0.07 | s–vs |
| 3.31 ± 0.06 | w |
| 3.21 ± 0.06 | w |
| 3.12 ± 0.06 | w |
| 3.07 ± 0.06 | w |
| 2.83 ± 0.05 | w |
| 2.78 ± 0.05 | w |
| 2.69 ± 0.05 | w |
| 2.47 ± 0.05 | w |
| 2.42 ± 0.05 | w |
| 2.38 ± 0.05 | w |

These X-ray diffraction data were collected with a Scintag diffraction system, equipped with a germanium solid state detector, using copper K-alpha radiation. The diffraction data were recorded by step-scanning at 0.02 degrees of two-theta, where theta is the Bragg angle, and a counting time of 10 seconds for each step. The interplanar spacings, d's, were calculated in Angstrom units (A), and the relative intensities of the lines, $I/I_o$ is one-hundredth of the intensity of the strongest line, above background, were derived with the use of a profile fitting routine (or second derivative algorithm). The intensities are uncorrected for Lorentz and polarization effects. The relative intensities are given in terms of the symbols vs=very strong (60–100), s=strong (40–60), m=medium (20–40) and w=weak (0–20). It should be understood that diffraction data listed for this sample as single lines may consist of multiple overlapping lines which under certain conditions, such as differences in crystallographic changes, may appear as resolved or partially resolved lines. Typically, crystallographic changes can include minor changes in unit cell parameters and/or a change in crystal symmetry, without a change in the structure. These minor effects, including changes in relative intensities, can also occur as a result of differences in cation content, framework composition, nature and degree of pore filling, and thermal and/or hydrothermal history. Other changes in diffraction patterns can be indicative of important differences between materials, which is the case for comparing MCM-49 with similar materials, e.g. MCM-22 and PSH-3.

The significance of differences in the X-ray diffraction patterns of these materials can be explained from a knowledge of the structures of the materials. MCM-22 and PSH-3 are members of an unusual family of materials because, upon calcination, there are changes in the X-ray diffraction pattern that can be explained by a significant change in one axial dimension. This is indicative of a profound change in the bonding within the materials and not a simple loss of the organic material. The precursor members of this family can be clearly distinguished by X-ray diffraction from the calcined members. An examination of the X-ray diffraction patterns of both precursor and calcined forms shows a number of reflections with very similar position and intensity, while other peaks are different. Some of these differences are directly related to the changes in the axial dimension and bonding.

The present as-synthesized MCM-49 has an axial dimension similar to those of the calcined members of the family and, hence, there are similarities in their X-ray diffraction patterns. Nevertheless, the MCM-49 axial dimension is different from that observed in the calcined materials. For example, the changes in axial dimensions in MCM-22 can be determined from the positions of peaks particularly sensitive to these changes. Two such peaks occur at ~13.5 Angstroms and ~6.75 Angstroms in precursor MCM-22, at ~12.8 Angstroms and ~6.4 Angstroms in as-synthesized MCM-49, and at ~12.6 Angstroms and ~6.30 Angstroms in the calcined MCM-22. Unfortunately, the ~12.8 Angstroms peak in MCM-49 is very close to the intense ~12.4 Angstroms peak observed for all three materials, and is frequently not fully separated from it. Likewise, the ~12.6 Angstroms peak of the calcined MCM-22 material is usually only visible as a shoulder on the intense ~12.4 Angstroms peak. FIG. 1 shows the same segment of the diffraction patterns of precursor MCM-22, calcined MCM-22, and MCM-49; the position of the ~6.6–6.3 Angstroms peak is indicated in each segment by an asterisk. Because the ~6.4 Angstroms peak is unobscured in MCM-49, it was chosen as a better means of distinguishing MCM-49 from the calcined forms of MCM-22 and PSH-3 rather than the much stronger ~12.8 Angstroms peak. Table I lists all diffraction peaks characteristic of MCM-49.

When used as a catalyst, the crystalline material of the invention may be subjected to treatment to remove part or all of any organic constituent. The crystalline material can also be used as a catalyst in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such component can be in the composition by way of cocrystallization, exchanged into the composition to the extent a Group IIIA element, e.g. aluminum, is in the structure, impregnated therein or intimately physically admixed therewith. Such component can be impregnated in or on to it such as, for example, by, in the case of platinum, treating the silicate with a solution containing a platinum metal-containing ion. Thus, suitable platinum compounds for this purpose include chloroplatinic acid, platinous chloride and various compounds containing the platinum amine complex.

The above crystalline MCM-49 material can be transformed to another form by thermal treatment. This thermal treatment is generally performed by heating at a temperature of at least about 370° C. for at least 1 minute and generally not longer than 20 hours. While subatmospheric pressure can be employed for the thermal treatment, atmospheric pressure is desired for reasons of convenience. The thermal treatment can be performed at a temperature up to about 925° C. The thermally treated product, especially in its metal, hydrogen and ammonium forms, is particularly useful in the catalysis of certain organic, e.g. hydrocarbon, conversion reactions. Non-limiting examples of such reactions include those for which MCM-22 may be used as catalyst. Incorporated herein by reference for the descriptions of those particular conversion reactions are U.S. Pat. Nos. 4,954,325; 4,973,784; 4,992,611; 4,956,514; 4,962,250; 4,982,033; 4,962,257; 4,962,256; 4,992,606; 4,954,663; 4,992,615; 4,983,276; 4,982,040; 4,962,239; 4,968,402; 5,000,839; 5,001,296; 4,986,894; 5,001,295; 5,001,283; 5,012,033; 5,019,670; 5,019,665; 5,019,664; and 5,013,422.

MCM-49, when employed either as an adsorbent or as a catalyst in the present alkylation process should be dehydrated, at least partially. This can be done by heating to a temperature in the range of 200° C. to about 370° C. in an atmosphere such as air, nitrogen, etc. and at atmospheric, subatmospheric or superatmospheric pressures for between 30 minutes and 48 hours. Dehydration can also be performed at room temperature merely by placing the MCM-49 in a vacuum, but a longer time is required to obtain a sufficient amount of dehydration.

MCM-49 can be prepared from a reaction mixture containing sources of alkali or alkaline earth metal (M), e.g. sodium or potassium, cation, an oxide of trivalent element X, e.g. aluminum, an oxide of tetravalent element Y, e.g. silicon, directing agent (R), and water, said reaction mixture having a composition, in terms of mole ratios of oxides, within the following ranges:

| Reactants | Useful | Preferred |
| --- | --- | --- |
| $YO_2/X_2O_3$ | 12 to <35 | 18 to 31 |
| $H_2O/YO_2$ | 10 to 70 | 15 to 40 |
| $OH^-/YO_2$ | 0.05 to 0.50 | 0.05 to 0.30 |
| $M/YO_2$ | 0.05 to 3.0 | 0.05 to 1.0 |
| $R/YO_2$ | 0.2 to 1.0 | 0.3 to 0.5 |

In this synthesis method, if more than one X component is present, at least one must be present such that the $YO_2/X_2O_3$ molar ratio thereof is less than about 35. For example, if aluminum oxide and gallium oxide components are used in the reaction mixture, at least one of the $YO_2/Al_2O_3$ and $YO_2/Ga_2O_3$ molar ratios must be less than about 35. If only aluminum oxide has been added to the reaction mixture as a source of X, the $YO_2/Al_2O_3$ ratio must be less than about 35.

In the present synthesis method, the source of $YO_2$ must be comprised predominately of solid $YO_2$, for example at least about 30 wt. % solid $YO_2$ in order to obtain the crystal product of the invention. Where $YO_2$ is silica, the use of a silica source containing at least about 30 wt. % solid silica, e.g. Ultrasil (a precipitated, spray dried silica containing about 90 wt. % silica) or HiSil (a precipitated hydrated $SiO_2$ containing about 87 wt. % silica, about 6 wt. % free $H_2O$ and about 4.5 wt. % bound $H_2O$ of hydration and having a particle size of about 0.02 micron) favors crystalline MCM-49 formation from the above mixture. Preferably, therefore, the $YO_2$, e.g. silica, source contains at least about 30 wt. % solid $YO_2$, e.g. silica, and more preferably at least about 40 wt. % solid $YO_2$, e.g. silica.

Directing agent R is selected from the group consisting of cycloalkylamine, azacycloalkane, diazacycloalkane, and mixtures thereof, alkyl comprising from 5 to 8 carbon atoms. Non-limiting examples of R include cyclopentylamine, cyclohexylamine, cycloheptylamine, hexamethyleneimine, heptamethyleneimine, homopiperazine, and combinations thereof.

Crystallization of the present crystalline material can be carried out at either static or stirred conditions in a suitable reactor vessel, such as for example, polypropylene jars or teflon lined or stainless steel autoclaves. The total useful range of temperatures for crystallization is from about 80° C. to about 225° C. for a time sufficient for crystallization to occur at the temperature used, e.g. from about 24 hours to about 60 days. Thereafter, the crystals are separated from the liquid and recovered.

It should be realized that the reaction mixture components can be supplied by more than one source. The reaction mixture can be prepared either batchwise or continuously.

Crystal size and crystallization time of the new crystalline material will vary with the nature of the reaction mixture employed and the crystallization conditions.

Synthesis of the new crystals may be facilitated by the presence of at least 0.01 percent, preferably 0.10 percent and still more preferably 1 percent, seed crystals (based on total weight) of crystalline product. Useful seed crystals include MCM-22 and/or MCM-49.

The MCM-49 crystals thus prepared can be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

MCM-49 may be incorporated with another material resistant to the temperatures and other conditions employed in organic conversion processes. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with MCM-49, i.e. combined therewith or present during synthesis of the new crystal, which is active, tends to change the conversion and/or selectivity of the catalyst in certain organic conversion processes. Inactive materials suitably serve as diluents to control the amount of conversion in a given process so that products can be obtained economically and orderly without employing other means for controlling the rate of reaction. These materials may be incorporated into naturally occurring clays, e.g. bentonite and kaolin, to improve the crush strength of the catalyst under commercial operating conditions. Said materials, i.e. clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with MCM-49 include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with MCM-49 also include inorganic oxides, notably alumina.

In addition to the foregoing materials, the new crystal can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of finely divided crystalline material and inorganic oxide matrix vary widely, with the crystal content ranging from about 1 to about 90 percent by weight and more usually, particularly when the composite is prepared in the form of beads, in the range of about 2 to about 80 weight percent of the composite.

In order to more fully illustrate the nature of the invention and the manner of practicing same, the following examples are presented. In the examples, whenever sorption data are set forth for comparison of sorptive capacities for water, cyclohexane and/or n-hexane, they were Equilibrium Adsorption values determined as follows:

A weighed sample of the calcined adsorbant was contacted with the desired pure adsorbate vapor in an adsorption chamber, evacuated to less than 1 mm and contacted with 12 Torr of water vapor and 40 Torr of n-hexane or cyclohexane vapor, pressures less than the vapor-liquid equilibrium pressure of the respective adsorbate at 90° C. The pressure was kept constant (within about ±0.5 mm) by addition of adsorbate vapor controlled by a manostat during the adsorption period, which did not exceed about 8 hours. As adsorbate was adsorbed by the new crystal, the decrease in pressure caused the manostat to open a valve which admitted more adsorbate vapor to the chamber to restore the above control pressures. Sorption was complete when the pressure change was not sufficient to activate the manostat. The increase in weight was calculated as the adsorption capacity of the sample in g/100 g of calcined adsorbant. The new synthetic material of this invention always exhibits Equilibrium Adsorption values of greater than about 10 wt. % for water vapor, greater than about 4.3 wt. %, usually greater than about 7 wt. % for cyclohexane vapor and greater than about 10 wt. % for n-hexane vapor. These vapor sorption capacities are a notable distinguishing feature of the present crystalline material.

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of silica-alumina cracking catalyst taken as an Alpha of 1 (Rate Constant=0.016 sec$^{-1}$). The Alpha Test is described in U.S. Pat. No. 3,354,078; in the *Journal of Catalysis*, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, Vol. 61, p. 395.

U.S. Pat. No. 5,236,575 to Bennett et al. discloses the synthesis and characterization of the synthetic porous material MCM-49, and is incorporated by reference as if set forth at length herein for such synthesis procedures.

ILLUSTRATIVE EMBODIMENT - PROCESS FLOW

Referring now to the FIGURE, a $C_4$-rich olefinic feed flows through line 10 and splits between lines 12 and 14. At least a portion of the olefin-rich feed flows through line 12, preferably from about 10 to about 90%, more preferably from about 10 to about 20%, and most preferably about 15%, with the balance of the olefin-rich feed flowing through line 14.

Line 20, containing i-$C_4$ recycle and fresh i-$C_4$, joins line 12 to form line 16 upstream of the first alkylation stage 16, which contains a solid alkylation catalyst having the structure of MCM-49. The effluent from the first alkylation zone 30 flows through line 32 and mixes with the olefin-rich stream from line 14 to form the second alkylation stage charge stream in line 34.

Flowrates through lines 14 and 32 are controlled to meet a predetermined target I/O ratio within the range disclosed above, and typically about 6:1. The second alkylation zone effluent flows from zone 40 to a product recovery and recycle section (not shown) via line 42 for separation and purification of recycle isobutane and product alkylate for gasoline blending.

EXAMPLES

Examples 1–3 illustrate the solid-catalyzed alkylation step of the present process, the liquid Brønsted acid-catalyzed step of the present process, as well as the combined two-stage process.

Example 1

Example 1 demonstrates isoparaffin-olefin alkylation in a fixed bed reactor using MCM-49/$Al_2O_3$ catalyst. The reaction was carried out at 300° F. (149° C.) and 700 psig with a feedstock having an isobutane/n-butenes ratio of about 30:1 at weight hourly space velocity (based on olefin) of about 0.05 hr$^{-1}$. The acivity and product selectivity were determined by gas chromatographic analysis of the total product (captured in a pressurized vessel) using a fused silica capillary column (Alltech's Durabond DB-1). The average olefin conversion and alkylate yield in Example 1 were 98.5% and 1.52 g $C_5$+ alkylate/g olefin converted respectively.

Example 2 repeated the procedure of Example 1 using a feedstock having an isobutane:butenes ratio of 6:1.

The total captured product from Example 1 was then blended with fresh 2-butenes to prepare a feedstock having an isobutane:butene ratio of 6:1. This feedstock was used in Example 3.

The alkylation reactions of Examples 2 and 3 were carried out in a stirred reactor at 51° F. (11° C.) and 150 psig using sulfuric acid as the catalyst. The weight hourly space velocity (based on olefin) was 0.038 hr$^{-1}$. The acid to oil ratio in the reactor was 1.40 (v/v). The activity and product selectivity were determined by gas chromatographic analysis of the off-gas and liquid product using a fused silica capillary column (Alltech's Durabond DB-1).

The average olefin conversions in Examples 2 and 3 were 99.8% and 100%, respectively. The alkylate yields in Example 2 and 3 were 1.84 and 1.87 g $C_5$+ alkylate/g olefin converted, respectively.

Table A shows a comparison of the composition of feeds used in Examples 1–3. Table B shows a comparison of the composition of the resulting alkylate product in Examples 1–3.

TABLE A

| Alkylation Feed Composition (wt %) | | | |
|---|---|---|---|
| | Example 1 | Example 2 | Example 3 |
| $C_3$ | 0.14 | 0.43 | 0.54 |
| $C_3=$ | 0.06 | 0.19 | 0.19 |
| i-$C_4$ | 95.63 | 81.95 | 77.61 |
| n-$C_4$ | 0.91 | 3.82 | 4.52 |
| $C_4=$ | 3.15 | 13.32 | 13.63 |
| $C_5$–$C_8$ | 0.12 | 0.29 | 3.51 |
| Total | 100.0 | 100.0 | 100.0 |

TABLE B

| Alkylate Product Composition (wt %) | | | |
|---|---|---|---|
| | Example 1 | Example 2 | Example 3 |
| $C_5$+ Alkylate (wt %) | | | |
| $C_5$ | 10.0 | 5.0 | 4.9 |
| $C_6$ | 11.5 | 5.6 | 5.6 |
| $C_7$ | 4.7 | 5.7 | 5.4 |

TABLE B-continued

Alkylate Product Composition (wt %)

| | Example 1 | Example 2 | Example 3 |
|---|---|---|---|
| $C_8$ | 59.0 | 71.9 | 73.0 |
| $C_9+$ | 14.8 | 11.8 | 11.1 |
| Total | 100.0 | 100.0 | 100.0 |

Total $C_8$ Composition (wt %)

| | Example 1 | Example 2 | Example 3 |
|---|---|---|---|
| 2,2,4-Trimethylpentane (TMP) | 6.0 | 34.4 | 33.6 |
| 2,2,3-Trimethylpentane (TMP) | 1.0 | 0.0 | 0.0 |
| 2,3,4-Trimethylpentane (TMP) | 31.9 | 25.6 | 24.6 |
| 2,3,3-Trimethylpentane (TMP) | 29.1 | 24.1 | 25.3 |
| 2,5-Dimethylhexane (DMH) | 2.3 | 5.4 | 4.8 |
| 2,4-Dimethylhexane (DMH) | 6.8 | 5.6 | 5.9 |
| 2,3-Dimethylhexane (DMH) | 14.1 | 4.2 | 4.8 |
| 3,4-Dimethylhexane (DMH) | 0.7 | 0.6 | 0.7 |
| Unknown $C_8$s | 8.1 | 0.1 | 0.3 |
| Total | 100.0 | 100.0 | 100.0 |
| TMP/DMH | 2.9 | 5.3 | 5.2 |

Comparing Examples 1 and 3 illustrates the advantage of the two-step alkylation process of the invention (using MCM-49 in the first alkylation stage and sulfuric acid in the second alkylation stage) in comparison with MCM-49 only. The two-step alkylation not only reduces $C_9+$ in the alkylate product from the MCM-49 alkylation, but further reduces the production of unknown $C_8$ components, thus improving alkylate yield. The TMP/DMH ratio, a measure of alkylate quality, increases in the second stage.

Comparing Examples 2 and 3 shows the advantage of the two-step alkylation over the sulfuric acid alkylation alone. In the two-step alkylation, the alkylate contains lower amounts of the undesirable $C_9+$ fraction, and higher amounts of the desirable $C_8$ fraction.

Changes and modifications in the specifically described embodiments can be carried out without departing from the scope of the invention which is intended to be limited only by the scope of the appended claims.

We claim:

1. A process for alkylating an isoparaffin with an olefin comprising the steps of:
   (a) reacting an isoparaffin having from 4 to 8 carbon atoms with an olefin having from 2 to 12 carbon atoms in a first alkylation reaction stage at temperature from about −40° C. to about 500° C. and overall isoparaffin:olefin feed weight ratio of from about 1:1 to about 250:1 with a solid alkylation catalyst comprising a synthetic porous crystalline material characterized by an X-ray diffraction pattern including values substantially as set forth in Table I of the specification and having a composition comprising the molar relationship $$X_2O_3:(n)YO_2,$$

wherein n is less than about 35, X is a trivalent element selected from the group consisting of Al, B, Fe, and Ga and Y is a tetravalent element selected from the group consisting of Si and Ge;

(b) mixing the effluent from said first alkylation stage with additional olefin to evolve an intermediate stream having an isoparaffin:olefin weight ratio of from about 2:1 to about 100:1; and
   (c) reacting said intermediate stream in a second alkylation stage in the absence of intermediate fractionation with a liquid acid catalyst comprising $H_2SO_4$ to produce $C_5+$ alkylate.

2. The process of claim 1 wherein said synthetic porous crystalline material has the structure of MCM-49.

3. The process of claim 1 wherein n is from about 10 to less than about 35.

4. The process of claim 3 wherein n is from about 15 to about 31.

5. The process of claim 1 wherein said porous synthetic material has a composition, on an anhydrous basis and in terms of moles of oxides per n moles of $YO_2$, expressed by the formula:

$$(0.1–0.6)M_2O:(1–4)R:X_2O_3:nYO_2$$

wherein M is alkali or alkaline earth metal and R is an organic moiety.

6. The process of claim 5 wherein said R is selected from the group consisting of cycloalkylamine, azacycloalkane, diazacycloalkane, and mixtures thereof.

7. The process of claim 5 wherein said crystalline material has original cations replaced, at least in part, with a cation or a mixture of cations selected from the group consisting of hydrogen and hydrogen precursors, rare earth metals, and metals of Groups IIA, IIIA, IVA, IB, IIB, IIIB, IVB, VIB and VIII of the Periodic Table of the Elements.

8. The process of claim 1 wherein X comprises aluminum and Y comprises silicon.

9. The process of claim 1 wherein X comprises gallium and Y comprises silicon.

10. The process of claim 3 wherein X comprises aluminum and Y comprises silicon.

11. The process of claim 4 wherein X comprises aluminum and Y comprises silicon.

12. The process of claim 7 wherein said replacing cations comprise hydrogen or a hydrogen precursor.

13. The process of claim 7 wherein said replacing cations comprise metals.

14. A process of claim 1 wherein said crystalline material is composited in a matrix.

15. The process of claim 14 wherein said matrix comprises alumina, silica, zirconia, titania, magnesia, beryllia or a combination thereof.

16. The process of claim 1 wherein said first alkylation stage effluent is mixed with an olefinic charge before contacting said liquid acid catalyst of step (b).

17. The process of claim 1 further comprising providing separate olefin-rich and isoparaffin-rich feedstream, and charging a major portion of said olefin-rich feedstream to said second alkylation stage.

18. The process of claim 1 wherein all isoparaffin charged to said second alkylation stage first passes through said first alkylation stage.

19. The process of claim 1 wherein the effluent from said second alkylation stage is recovered in a fractionation system into at least alkylate and an isoparaffin-rich recycle stream which recycle stream is then charged back to said first stage reactor.

20. The process of claim 19 wherein said recycle stream is treated to provide a substantially acid-free recycle to said first alkylation reaction stage.

21. The process of claim 1 wherein said overall isoparaffin:olefin weight ratio in the feed to said first alkylation stage is from about 10:1 to about 50:1 and said additional olefin of step (b) is added at a rate sufficient to evolve an intermediate stream having an isoparaffin:olefin weight ratio of from about 2:1 to about 10:1.

* * * * *